(12) United States Patent
Brunfeld et al.

(10) Patent No.: US 7,193,725 B2
(45) Date of Patent: Mar. 20, 2007

(54) METHOD AND SYSTEM FOR OPTICAL MEASUREMENT VIA A RESONATOR HAVING A NON-UNIFORM PHASE PROFILE

(75) Inventors: Andrei Brunfeld, Cupertino, CA (US); Bryan Clark, Mountain View, CA (US)

(73) Assignee: Xyratex Technology Ltd., Hampshire (GB)

( * ) Notice: Subject to any disclaimer, the term of this patent is extended or adjusted under 35 U.S.C. 154(b) by 557 days.

(21) Appl. No.: 10/770,866

(22) Filed: Feb. 2, 2004

(65) Prior Publication Data

US 2004/0156085 A1 Aug. 12, 2004

Related U.S. Application Data

(63) Continuation-in-part of application No. 10/403,238, filed on Mar. 28, 2003, now Pat. No. 6,778,307, which is a continuation-in-part of application No. 09/789,913, filed on Feb. 21, 2001, now Pat. No. 6,522,471.

(51) Int. Cl.
*G01B 9/02* (2006.01)
(52) U.S. Cl. ...................... 356/519; 356/511
(58) Field of Classification Search .............. 356/519, 356/511, 512
See application file for complete search history.

(56) References Cited

U.S. PATENT DOCUMENTS

| | | | | |
|---|---|---|---|---|
| 6,522,471 | B2 * | 2/2003 | Clark | 356/519 |
| 6,653,649 | B2 * | 11/2003 | Clark | 356/519 |
| 6,717,707 | B2 * | 4/2004 | Clark | 356/519 |
| 6,778,307 | B2 * | 8/2004 | Clark | 356/519 |
| 2005/0236589 | A1 * | 10/2005 | Brunfeld et al. | 250/559.11 |

\* cited by examiner

*Primary Examiner*—Gregory J. Toatley, Jr.
*Assistant Examiner*—Patrick Connolly
(74) *Attorney, Agent, or Firm*—A. Mitchell Harris; Jeffrey D. Moy; Weiss & Moy, P.C.

(57) ABSTRACT

A method and system for optical measurement via a resonator having a non-uniform phase profile provides a mechanism for measuring and/or detecting sub-micron surface features with increased resolution. A second surface forming part of a resonator is illuminated through a first partially reflective surface that has a non-uniform phase profile that transitions from negative to positive phase with respect to a resonance phase value of the resonator. As a result, a reduced spot size is produced at the second surface, which enhances the resolution of a measurement and/or detection of surface features on the second surface. Additionally, if a discontinuity is provided in the non-uniform phase profile, interaction of the discontinuity with surface features of the second surface will provide enhanced resolution of the surface features. The resolution of the system is improved over the resolution that can be attained using a Fabry-Perot resonator.

19 Claims, 7 Drawing Sheets

METHOD AND SYSTEM FOR OPTICAL MEASUREMENT VIA A RESONATOR HAVING A NON-UNIFORM PHASE PROFILE

CROSS-REFERENCE TO RELATED APPLICATIONS

This application is a Continuation-in-part of U.S. patent application Ser. No. 10/403,238, now U.S. Pat. No. 6,778, 307, entitled "METHOD AND SYSTEM FOR PERFORMING SWEPT-WAVELENGTH MEASUREMENTS WITHIN AN OPTICAL SYSTEM", filed on Mar. 28, 2003, which is a Continuation-in-part of U.S. patent application Ser. No. 09/789,913, now U.S. Pat. No. 6,522,471 filed Feb. 21, 2001, from which it claims benefit of priority under 35 U.S.C. § 120. The specifications of the above-referenced patent applications are incorporated herein by reference. A parent application of above-incorporated Patent Application entitled "OPTICAL MEASUREMENT AND INSPECTION METHOD AND APPARATUS HAVING ENHANCED OPTICAL PATH DIFFERENCE DETECTION" issued as U.S. Pat. No. 6,653,649 and is incorporated herein by reference. The present application is also related to U.S. patent application Ser. No. 10/644,243 entitled "METHOD AND APPARATUS INCLUDING IN-RESONATOR IMAGING LENS FOR IMPROVING RESOLUTION OF A RESONATOR-ENHANCED OPTTCAL SYSTEM" and filed on Aug. 20, 2003, the specification of which is also incorporated reference.

BACKGROUND OF THE INVENTION

1. Field of the Invention

This invention relates to optical measurement systems, and more specifically, to a method and system for optical measurement using a resonator incorporating a non-uniform phase characteristic.

2. Description of the Related Art

Present-day wafer patterns, optical circuits, and other microstructures are manufactured with features smaller than the optical wavelength and are sometimes referred to as "sub-micron" or "nanometric" technologies. In the manufacturing process, it is necessary to inspect small structures, to determine whether or not they are manufactured to the tolerances demanded by functional requirements and to make necessary adjustments in the manufacturing process to avoid manufacturing defective components.

In addition to optical and electronic integrated circuits, optical devices such as diffraction gratings and photographic masks such as the one used in photolithography, as well as the photolithographic patterns have sub-micron feature sizes and also must be measured and/or inspected for proper manufacturing tolerances and to determine if errors are present in the photographic masks. Also, biological structures encountered in microbiological studies require detection and measurement of very small shapes having small height variation.

In order to measure the above-mentioned sub-micron structures, scanning microscopy techniques are typically used, including near-field optical microscopy. Resolving small features is not possible with typical far-field techniques, due to the interaction of the feature edges that each produce a diffracted beam. The diffracted field expands in a manner inversely proportional with the size of the structures and the diffracted beams from each of the features then interfere during the field propagation. The contribution from each of the discrete edges cannot be separated, causing the "diffraction limitations" well known in optical systems. The above-incorporated Patent Application and Patent disclose methodologies and systems for making optical measurements using resonators to enhance the resolution of the measurement beyond the limitations of traditional microscopy, by reducing the impact of diffraction on the measurement through introduction of a resonance in the measurement path.

However, even with resonator enhancement, diffraction still places a limitation on the resolution of an optical measurement system. Therefore, it would be desirable to further enhance the resolution of a resonator-enhanced optical measurement system.

SUMMARY OF THE INVENTION

The foregoing objectives are achieved in an optical measuring system and method for optical measuring. The measurement system includes an optical illumination system for producing an optical beam, a resonator positioned within a path of the beam and a detector for detecting an intensity of light leaving the resonator. The resonator includes a non-uniform phase profile on a first surface of the resonator so that a beam with a reduced spot size is produced on the second surface of the resonator. The spot size of the beam is decreased over that of a Fabry-Perot resonator, due to the phase profile of the first surface, which transitions from a negative phase to positive phase with respect to the resonance phase value of the resonator.

The non-uniform phase profile may be a step or other discontinuity in the first surface or the first surface may be shaped to provide a more gradual phase progression.

A scanning system may be employed to move the first surface across a surface of interest that forms the second surface of the resonator, providing a scanning surface measurement system having enhanced resolution, either due to the reduced spot size or via an interaction of a phase discontinuity with surface features of the surface of interest. The surface features may be surface features of a surface under measurement or may be data-bearing features of an optical storage medium such as optical disc media.

The foregoing and other objects, features, and advantages of the invention will be apparent from the following, more particular, description of the preferred embodiment of the invention, as illustrated in the accompanying drawings.

DESCRIPTION OF THE PREFERRED EMBODIMENTS

The above-incorporated Patent and Patent Applications disclose a variety of optical systems and features of optical systems using a Fabry-Perot resonator to improve the resolution of the optical systems. The Fabry-Perot provides improved performance by reducing the spot size of illumination within a resonator that includes the surface of interest within the resonator. By various tuning mechanisms, the Fabry-Perot resonator is tuned to particular operating points to achieve either a narrowed illumination beam, increased resonator sensitivity and/or enhanced selectivity within the measurement.

The present invention concerns an improvement to the above-mentioned Fabry-Perot-enhanced optical systems. A non-uniform illumination phase profile is introduced by modifying at least one surface of the resonator. The non-uniform phase profile further narrows the illumination within the resonator, further enhancing the resolution and other performance characteristics of the optical system, such as sensitivity in applications where the resonator is tuned to the slope of the response curve.

Figure 1:
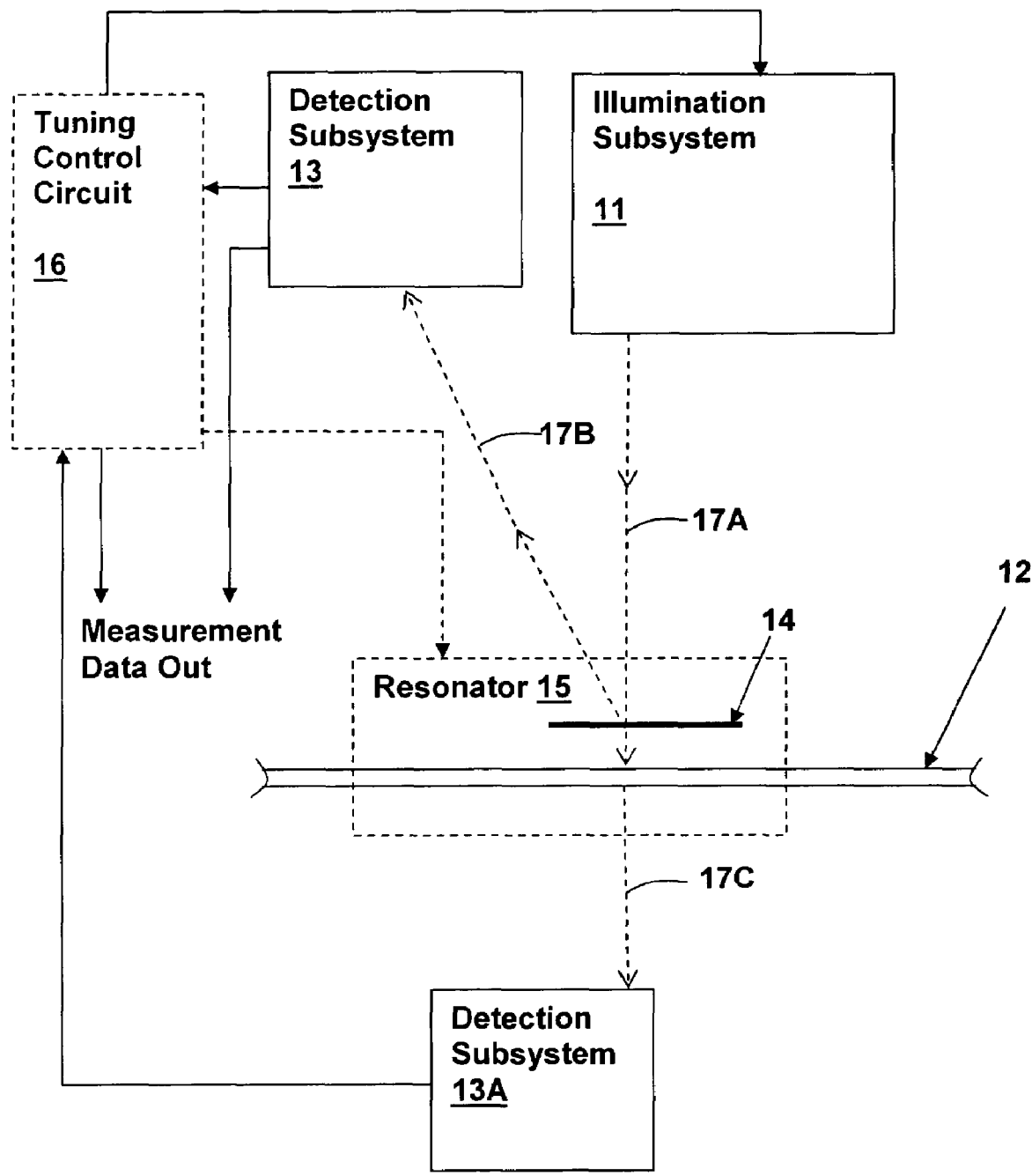
FIG. 1 is an illustration depicting an optical system in accordance with an embodiment of the present invention.

With reference now to the figures, and particularly to FIG. 1, a surface or volume 12 including features under detection or data that is being extracted is illuminated by an illumination beam 17A. Surface or volume 12 may be an optical device, integrated circuit, patterned wafer, lithographic mask, biological organism, or other structure having sub-micron features that would typically be measurable only with near-field probing techniques.

A resonator 15 is formed by a partially reflective surface 14 positioned within the optical path of the illumination beam 17A and is tuned at a predetermined operating point to provide the desired characteristics at detection subsystem 13 and/or 13A. A reflected beam 17B and/or a transmitted beam 17C leaving resonator 15 is detected by a detection subsystem 13 and/or 13A, providing measurement information or data extraction. The predetermined resonator optical length may be maintained with control signals from tuning control circuit 16 acting mechanically (in general piezo-movement) on the partially reflective surface 14, by introducing an optical retarder in the illumination beam (e.g. an electro-optical liquid or crystal), or by controlling the frequency (wavelength) of illumination system 11. Without limitation with respect to the specific manner of optical resonance control provided, the control, if employed is performed in response to signals from tuning control circuit 16. Either mechanism or a combination may be used to maintain the resonance operating point of resonator 15. Alternatively or in concert, tuning control circuit 16 may provide a swept-wavelength illumination by tuning a wavelength of illumination subsystem 11 as described in the above-referenced Patent Application "METHOD AND SYSTEM FOR PERFORMING SWEPT-WAVELENGTH MEASUREMENTS WITHIN AN OPTICAL SYSTEM."

Detection subsystem 13 may provide information to tuning control circuit 16 so that deviations from the resonance operating point can be detected, which is generally a deviation from an intensity level (which may be "dark" or "gray" level) of an interferometric fringe detection (e.g., a dark level detector located at one of the fringe lines formed inside the resonator and detected in one of beams 17B or 17C). Measurement data or data extraction may be produced by detection subsystem 13 and/or 13A or by extracting components of the feedback control signals from tuning control circuit 16 or both the direct detection output along with the feedback sources of information may be processed and used.

The apparatus of the present invention incorporates a non-uniform phase distribution generated by a reference surface forming part of partially reflective surface (or otherwise introduced within the illumination path within resonator 15) that is introduced between surface or volume of interest 12 and illumination beam 17A. Either the surface or volume of interest 12 may be moved under the optical measurement system or the optical measurement system may be moved over surface or volume of interest 12.

The non-uniform phase distribution incorporated within resonator 15 may be generally continuous or discontinuous. In either case, the phase distribution and position of partially reflective surface 14 are generally selected so that the phase distribution passes through a resonance phase point with a negative phase on one side and positive phase on the other side of a line dividing a positive half-plane and a negative half-plane of the resonant surface, although other phase distributions may be employed. The interaction of illumination passing through the two half-planes with the second surface of resonator 15 (e.g., a surface of surface or volume of interest 12) provides a smaller illumination spot size on the second surface, as well as a increased sharpness of the illumination (steeper beamwidth). If the phase distribution is discontinuous, e.g. a step in phase is introduced, then the step may further interact with surface features being measured, providing a reference point for the measurement and permitting measurement of structures having feature sizes smaller than the diffraction limit.

Figure 2A:
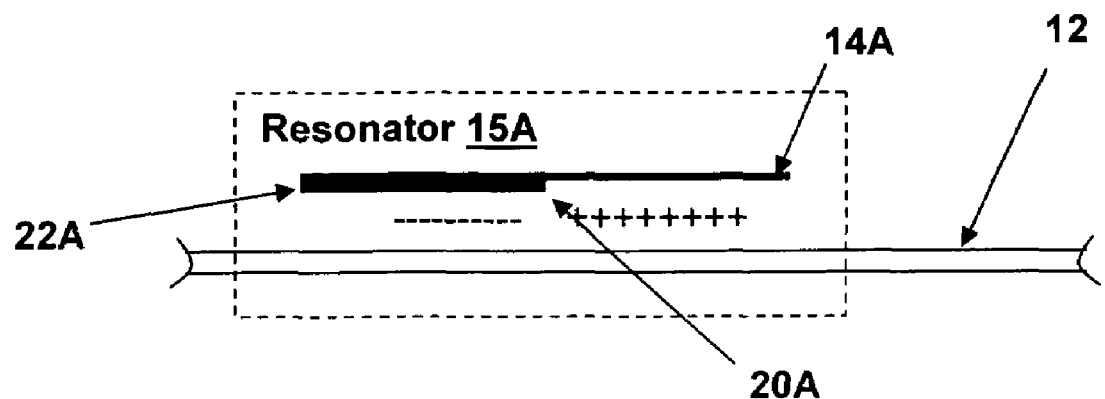
FIG. 2A is a pictorial diagram showing details of a resonator as may be employed in the optical system of FIG. 1
Figure 2B:
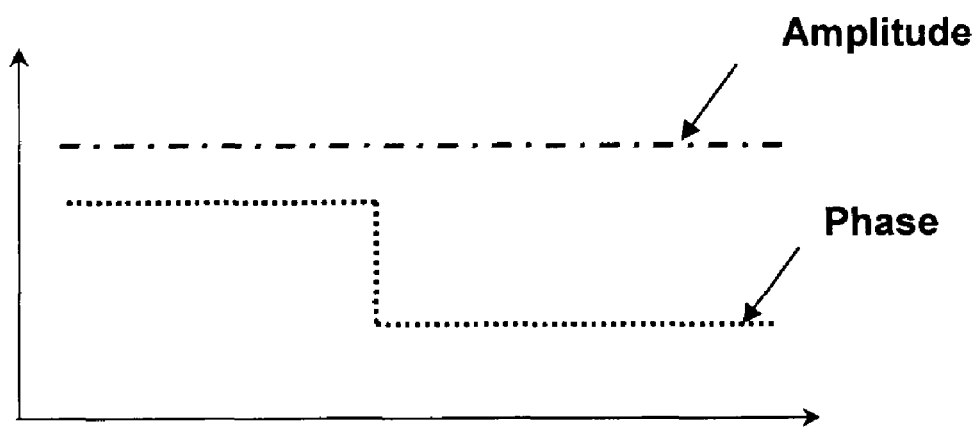
FIG. 2B is a graph depicting optical characteristics of the resonator of FIG. 2A.

Referring now to FIGS. 2A and 2B, a resonator 15A is described as may be used for resonator 15 within the optical system of FIG. 1. Resonator 15A includes a partially reflective surface 14A provided on the upper side of a reference structure 22A having a step 20A in thickness on a lower side thereof. Step 20A thereby introduces a phase difference between the left half-plane (negative phase) and right half-plane (positive phase) of illumination passing through partially reflective surface 14A since reference structure 22A has a refractive index greater than the surrounding medium (typically air). FIG. 2B shows the amplitude and phase profiles of the illumination leaving the bottom surfaces of reference structure 22A.

Figure 3A:
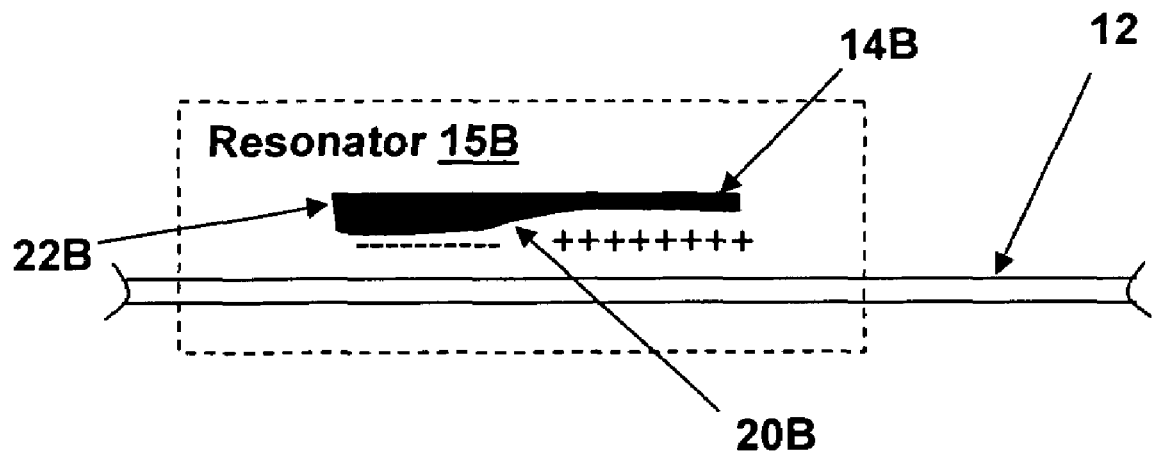
FIG. 3A is a pictorial diagram showing details of another resonator as may be employed in the optical system of FIG. 1
Figure 3B:
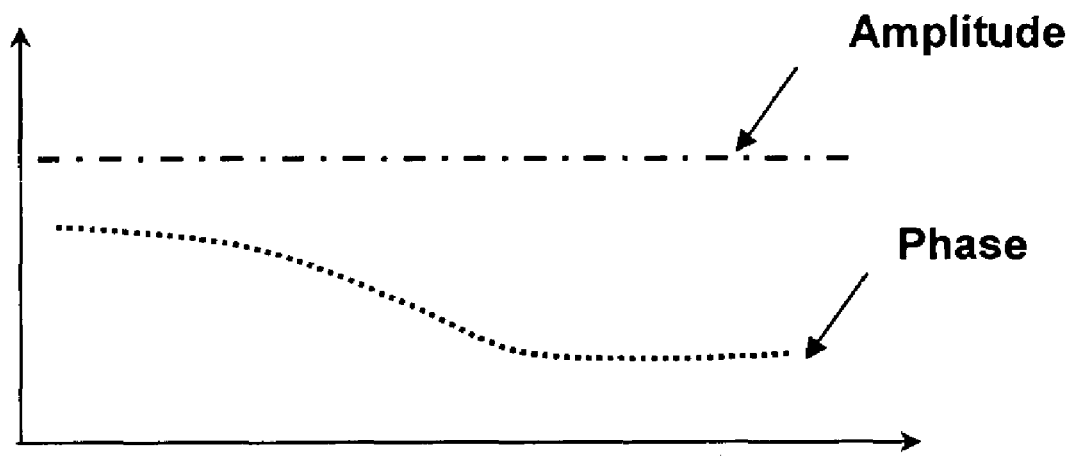
FIG. 3B is a graph depicting optical characteristics of the resonator of FIG. 3A.

Referring now to FIGS. 3A and 3B, another resonator 15B is described as may be used for resonator 15 within the optical system of FIG. 1. Resonator 15B includes a partially reflective surface 14B provided on the upper side of a reference structure 22B having a curved lower surface 20B on a lower side thereof, which alters the thickness of reference structure 22B. Curved surface 20B thereby introduces a phase difference and variation between the left half-plane (negative phase) and right half-plane (positive phase) of illumination passing through partially reflective surface 14B since reference structure 22B has a refractive index greater than the surrounding medium (typically air).

FIG. 3B shows the amplitude and phase profiles of the illumination leaving the bottom surface of reference structure 22B.

Figure 4A:
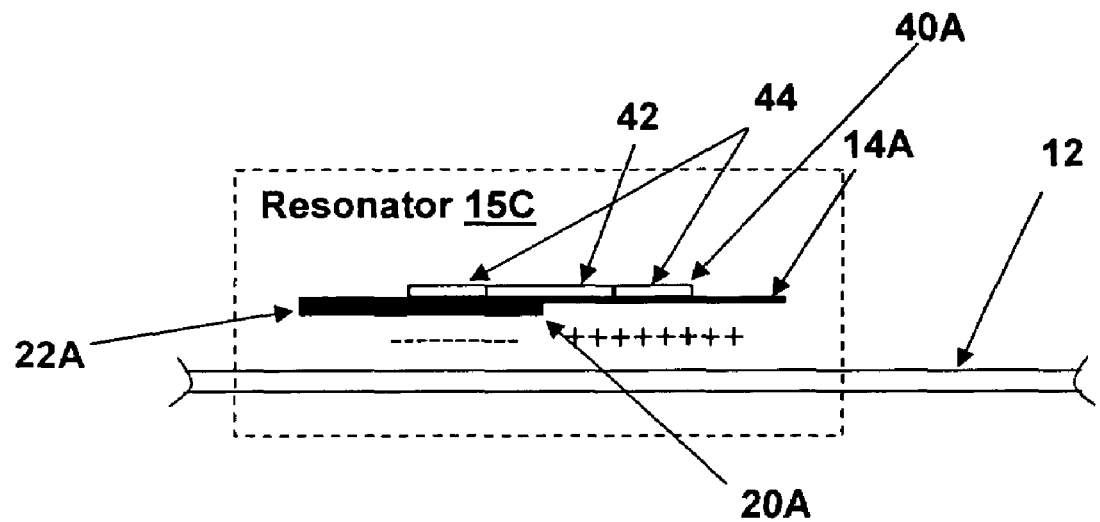
FIG. 4A is a pictorial diagram showing details of yet another resonator as may be employed in the optical system of FIG. 1
Figure 4B:
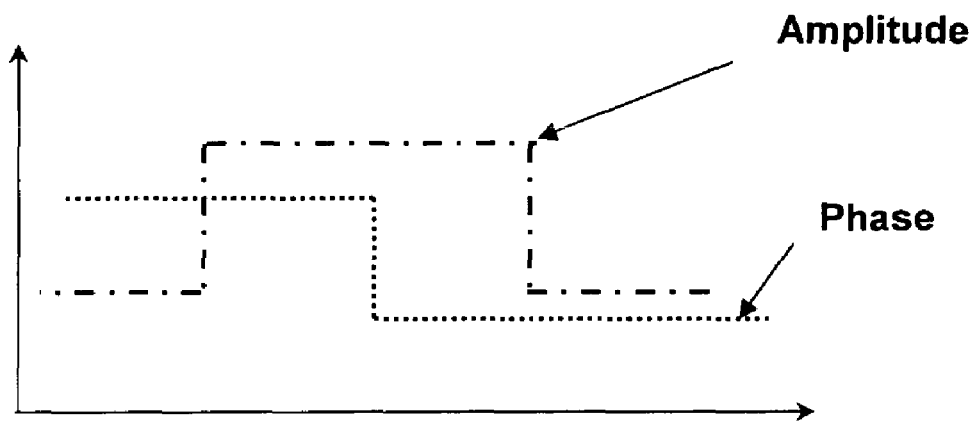
FIG. 4B is a graph depicting optical characteristics of the resonator of FIG. 4A.

Referring now to FIGS. 4A and 4B, yet another resonator 15C is described as may be used for resonator 15 within the optical system of FIG. 1. Resonator 15C includes a partially reflective surface and reference structure as described for resonator 15A of FIG. 2A, but in addition, incorporates a mask 40A that introduces an amplitude step in each half-plane that can be used to further tune the spot size and sharpness of the illumination leaving reference structure 22A. FIG. 4B shows the amplitude and phase profiles of the illumination leaving the bottom surfaces of reference structure 22A. Mask 40A has an annular pattern 44 that is less transmissive than a central portion 42, providing the amplitude profile seen in FIG. 4B.

Figure 5A:
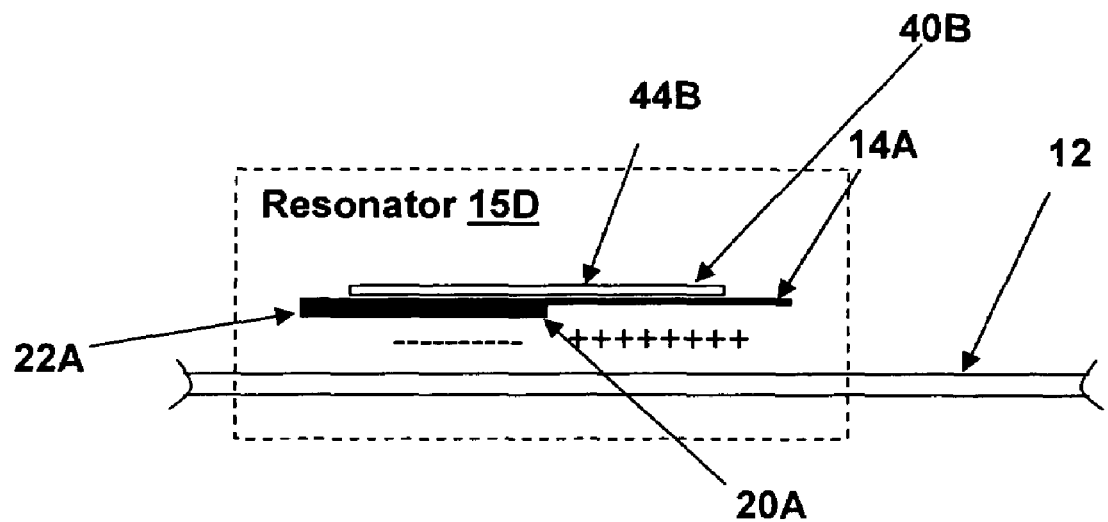
FIG. 5A is a pictorial diagram showing details of still another resonator as may be employed in the optical system of FIG. 1
Figure 5B:
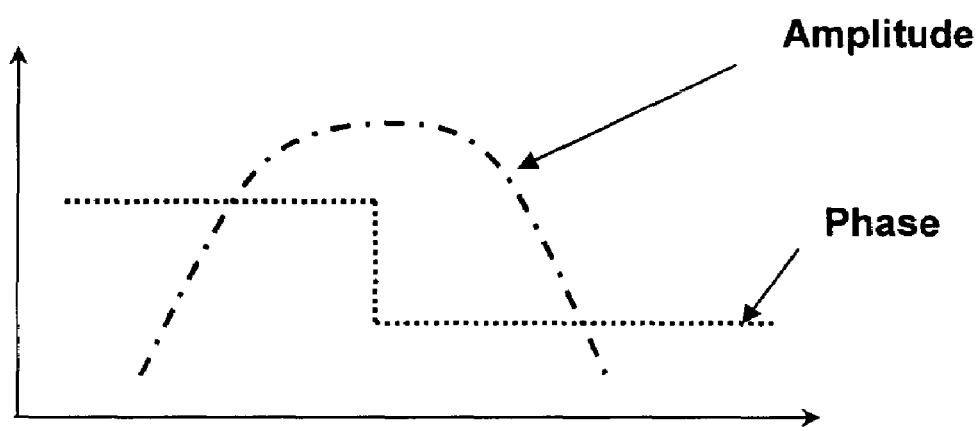
FIG. 5B is a graph depicting optical characteristics of the resonator of FIG. 5A.

Referring now to FIGS. 5A and 5B, yet another resonator 15D is described as may be used for resonator 15 within the optical system of FIG. 1. Resonator 15D includes a partially reflective surface and reference structure as described for resonator 15A of FIG. 2A, but in addition, incorporates a filter 40B that introduces a gradual change in transmissivity via a coating 44B, that generates a decrease in amplitude extending outward from step 20A in each half-plane that can be used to further tune the spot size and sharpness of the illumination leaving reference structure 22A. FIG. 5B shows the amplitude and phase profiles of the illumination leaving the bottom surfaces of reference structure 22A. Coating 44B has an continuously varying transmissivity decreasing radially from the center above step 20A, providing the amplitude profile seen in FIG. 5B.

Figure 6A:
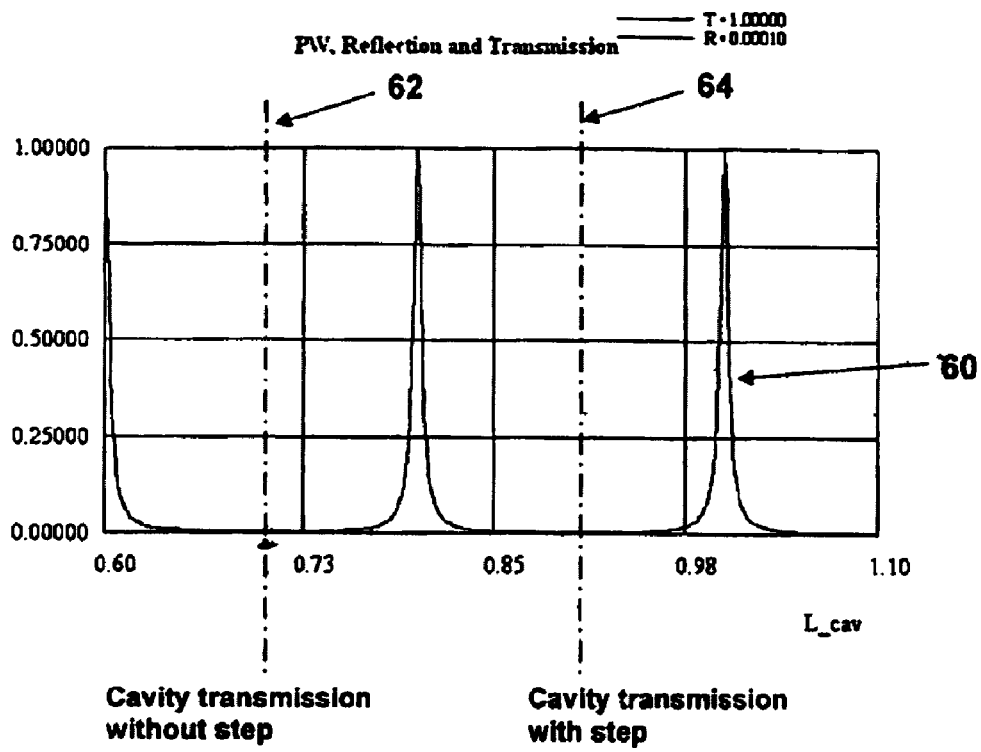
FIG. 6A is a graph depicting tuning points of portions of a resonator in accordance with an embodiment of the invention.

Referring now to FIG. 6A, tuning of the above described resonators is illustrated, as well as a principle of operation of the non-uniform phase profile. The description of operation will be directed toward a resonator incorporating a step in phase as embodied by resonator 15A of FIG. 2A, but it should be understood that the description applies in principle to all of the illustrated resonators and variations thereof. FIG. 6A shows a graph of resonator response 60 with cavity length. Line 62 indicates a cavity length without a step in reference structure 22A and line 64 indicates the cavity length with the step 22, as tuned for operation in accordance with an embodiment of the present invention. Since the transmission at both phase positions away from the step is zero, one phase point (at line 62) is in the region below a resonance and the other phase point is in the region above the resonance (at line 64). Therefore, near the center of the resonator, the field must pass through the resonance point, yielding an intensity peak.

Figure 6B:
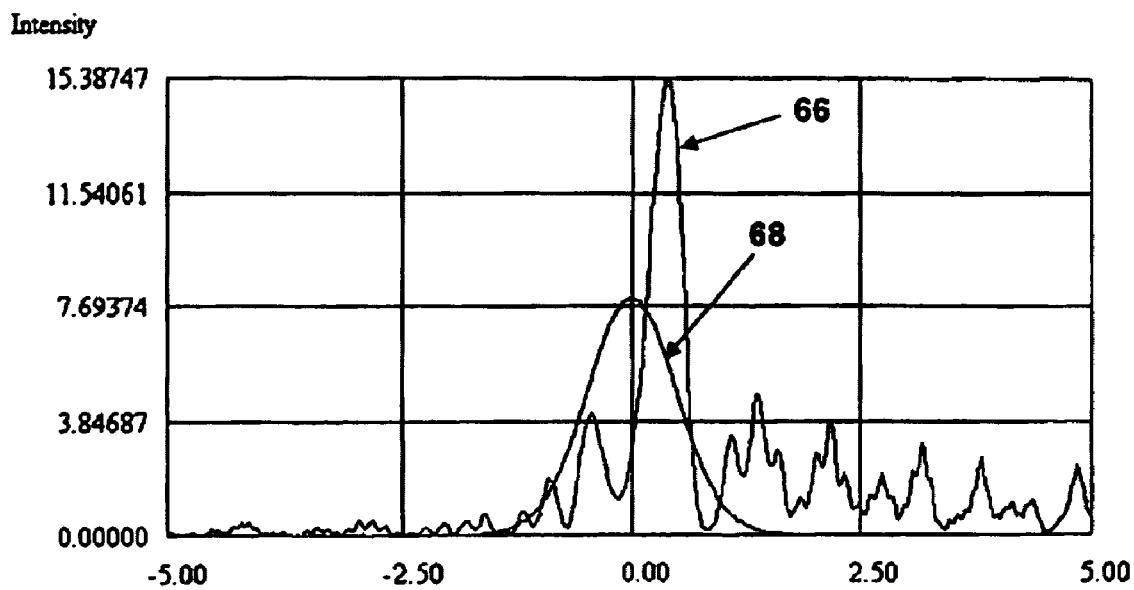
FIG. 6B is a graph depicting performance of a resonator in accordance with an embodiment of the invention.

FIG. 6B shows an amplitude response 68 of a resonator versus the radial displacement from the center of the beam for a typical Fabry-Perot resonator. Amplitude response 66 is the response of the stepped resonator 15A depicted in FIG. 2A, showing that the intensity of the spot, as well as spot size and sharpness (steepness of the curve on both sides of the main lobe) has increased dramatically. The result is increased resolution of measurement and optical data storage/retrieval systems employing the resonator of the present invention, which can extend to below the diffraction limit.

Figure 7A:
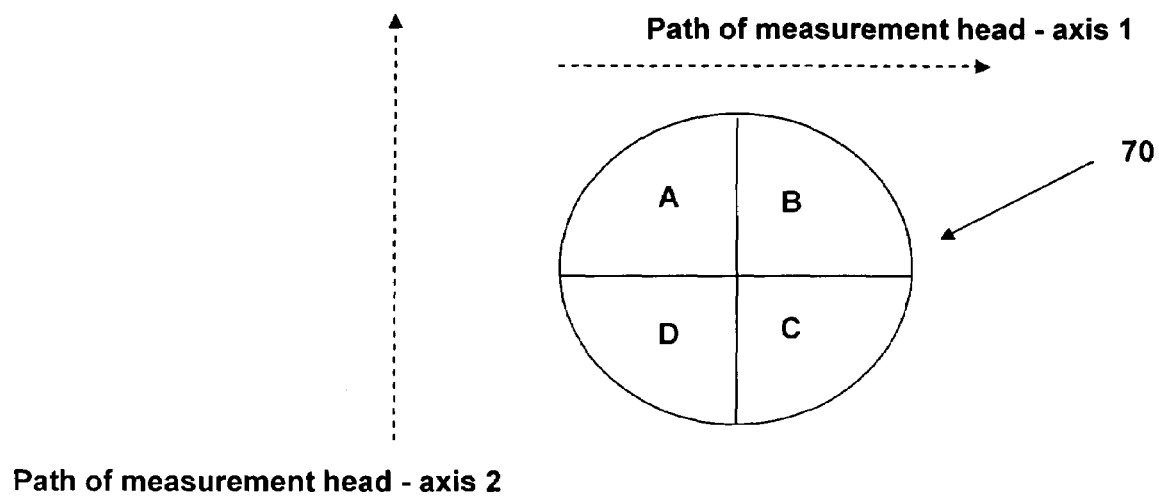
FIGS. 7A and 7B are top and side views, respectively, of a stepped surface as included in an optical measuring system in accordance with an alternative embodiment of the present invention.
Figure 7B:
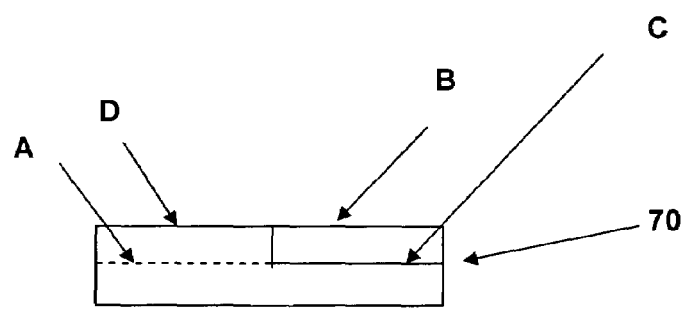

Referring now to FIG. 7A and FIG. 7B a top and a side view of a reference surface 70 in accordance with an alternative embodiment of the invention is depicted. Reference surface 70 may be included in a measurement system such as the optical measurement system of FIG. 1, with the addition of positioning in two axes rather than one. Axis 1 and Axis 2 motions are possible simultaneously or separately, to permit scanning of a surface in two dimensions.

Reference surface 70 includes a step in each of two axes (the measurement head motional axes as shown in the figure). The interaction of the steps resulting between the different quadrants defined by surfaces A, B, C, and D to interact with features in two scanning directions on or within a device under test. The differences in detected light produced by the interaction with edges of the features may be separated by processing the resulting detected intensities. In general, a reduced spot size in both axis can also be achieved, resulting in increased resolution in two dimensions.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical system comprising:
    an optical illumination system for producing a first beam for illuminating a surface of interest;
    a partially reflective surface positioned between said optical illumination system and said surface of interest and forming a resonator with said surface of interest, said partially reflective surface having a non-uniform phase profile that transitions from a negative phase to a positive phase with respect to a resonance phase value of said resonator, whereby a second beam having a spot size smaller than a spot size of said first beam is produced at said surface of interest; and
    a detector for measuring an amplitude of light leaving said resonator, whereby features of said surface of interest are detected.

2. The optical system of claim 1, wherein said non-uniform phase profile includes a phase discontinuity.

3. The optical system of claim 2, wherein said phase discontinuity is a step in said partially reflective surface.

4. The optical system of claim 1, wherein said non-uniform phase profile is provided by a curvature of said partially reflective surface.

5. The optical system of claim 1, wherein said partially reflective surface is provided on a planar refractive substrate, and wherein said non-uniform phase profile is provided by a change in refractive index of said refractive substrate.

6. The optical system of claim 1, wherein said non-uniform phase profile comprises two non-uniform phase profiles in orthogonal directions along said partially reflective surface, whereby detection of said surface features is improved in two dimensions along said surface of interest.

7. The optical system of claim 1, further comprising a scanning subsystem for moving a relative position of said partially reflective surface and said surface of interest in an axis parallel to a plane of said surface of interest, whereby said surface of interest is scanned for detecting said surface features.

8. The optical system of claim 1, wherein said surface of interest is an optical storage medium, wherein said surface features are data-bearing features, and further comprising a data decoder coupled to said detector for extracting data from said optical storage medium.

9. The optical system of claim 1, wherein said partially reflective surface further includes a non-uniform amplitude profile.

10. The optical system of claim 9, wherein said non-uniform amplitude profile includes an amplitude discontinuity.

11. A method for optical detection of features of a surface of interest, said method comprising:
   first illuminating a partially reflective surface with an illumination beam from an illumination subsystem;
   second illuminating a surface of interest with a beam transmitted from said partially reflective surface, said transmitted beam having characteristics introduced by a resonance between said partially reflective surface and said surface of interest and by a non-uniform phase profile of said partially reflective surface, wherein said non-uniform phase profile transitions from a negative phase to a positive phase with respect to a resonance phase value of said resonance; and
   moving one of said surface of interest and said partially reflective surface relative and substantially parallel to each other; and
   detecting an amplitude of light leaving said resonance, whereby variations in said amplitude provide detection of said surface features.

12. The method of claim 11, wherein said second illuminating illuminates said surface of interest through a phase discontinuity on said partially reflective surface.

13. The method of claim 12, wherein said phase discontinuity is a step in said partially reflective surface, and wherein said second illuminating illuminates said surface of interest through said step.

14. The method of claim 11, wherein said non-uniform phase profile is provided by a curvature of said partially reflective surface, and wherein said second illuminating illuminates said surface of interest through said curvature.

15. The method of claim 11, wherein said partially reflective surface is provided on a planar refractive substrate, wherein said non-uniform phase profile is provided by a change in refractive index of said refractive substrate, and wherein said second illuminating illuminates said surface of interest through said change in refractive index.

16. The method of claim 11, wherein said non-uniform phase profile comprises two non-uniform phase profiles in orthogonal directions along said partially reflective surface, and wherein whereby said detection of said surface features is improved in two dimensions along said surface of interest.

17. The method of claim 11, wherein said surface of interest is an optical storage medium, wherein said surface features are data-bearing features, and further comprising analyzing a result of said detecting for extracting data from said optical storage medium.

18. The method of claim 11, wherein said partially reflective surface further includes a non-uniform amplitude profile, and wherein said second illuminating further illuminates said surface of interest through said non-uniform amplitude profile.

19. The method of claim 18, wherein said non-uniform amplitude profile includes an amplitude discontinuity, and wherein said second illuminating further illuminates said surface of interest through said amplitude discontinuity.

* * * * *